(12) United States Patent
Siess et al.

(10) Patent No.: US 8,613,777 B2
(45) Date of Patent: Dec. 24, 2013

(54) METHOD FOR PERFORMING INTRAVASCULAR CARDIAC SURGERY

(75) Inventors: Thorsten Siess, Wuerselen (DE); Willem Flameng, Leuven (BE)

(73) Assignee: Abiomed Europe GmbH, Aachen (DE)

( * ) Notice: Subject to any disclaimer, the term of this patent is extended or adjusted under 35 U.S.C. 154(b) by 156 days.

(21) Appl. No.: 12/208,879

(22) Filed: Sep. 11, 2008

(65) Prior Publication Data

US 2009/0024212 A1     Jan. 22, 2009

Related U.S. Application Data

(62) Division of application No. 10/964,066, filed on Oct. 13, 2004, now abandoned, which is a division of application No. 09/890,778, filed as application No. PCT/EP00/00863 on Feb. 3, 2000, now abandoned.

(30) Foreign Application Priority Data

Feb. 6, 1999   (DE) .................................. 199 04 975

(51) Int. Cl.
    *A61F 2/72*     (2006.01)
(52) U.S. Cl.
    USPC ............................................................ 623/26
(58) Field of Classification Search
    USPC ............................................. 623/2.11, 1.26
    See application file for complete search history.

(56) References Cited

U.S. PATENT DOCUMENTS

| | | | |
|---|---|---|---|
| 5,163,910 A * | 11/1992 | Schwartz et al. | 604/151 |
| 5,376,114 A | 12/1994 | Jarvis | |
| 5,713,953 A * | 2/1998 | Vallana et al. | 623/2.15 |
| 5,855,597 A * | 1/1999 | Jayaraman | 623/1.16 |
| 6,245,102 B1 | 6/2001 | Jayaraman | |
| 6,248,091 B1 * | 6/2001 | Voelker | 604/96.01 |
| 6,425,916 B1 * | 7/2002 | Garrison et al. | 623/2.11 |
| 7,018,406 B2 | 3/2006 | Seguin et al. | |

* cited by examiner

Primary Examiner — Gary Jackson
Assistant Examiner — Eric Blatt
(74) Attorney, Agent, or Firm — Fulwider Patton LLP

(57) ABSTRACT

For the treatment of an insufficient cardiac valve or a cardiac valve with a stenosis, a device is provided that comprises a micro axial pump (40). The pump portion (14) of the micro axial pump carries a dilating device (18) suitable for pushing open a stenosis in a valve. The dilating device is designed as a high-pressure balloon. During dilation, the micro axial pump (40) operates so that the heart is relieved. With insufficient cardiac valves, a stent (21) is fastened to the dilating device (17), the stent surrounding a flexible cardiac valve prosthesis (20). By dilation, the stent (21) is pressed against the insufficient cardiac valve and the same is passivated. The cardiac valve of the cardiac valve prosthesis is unfolded to assume the function of the natural cardiac valve.

5 Claims, 5 Drawing Sheets

METHOD FOR PERFORMING INTRAVASCULAR CARDIAC SURGERY

CROSS-REFERENCE TO RELATED APPLICATION

Figure 1:
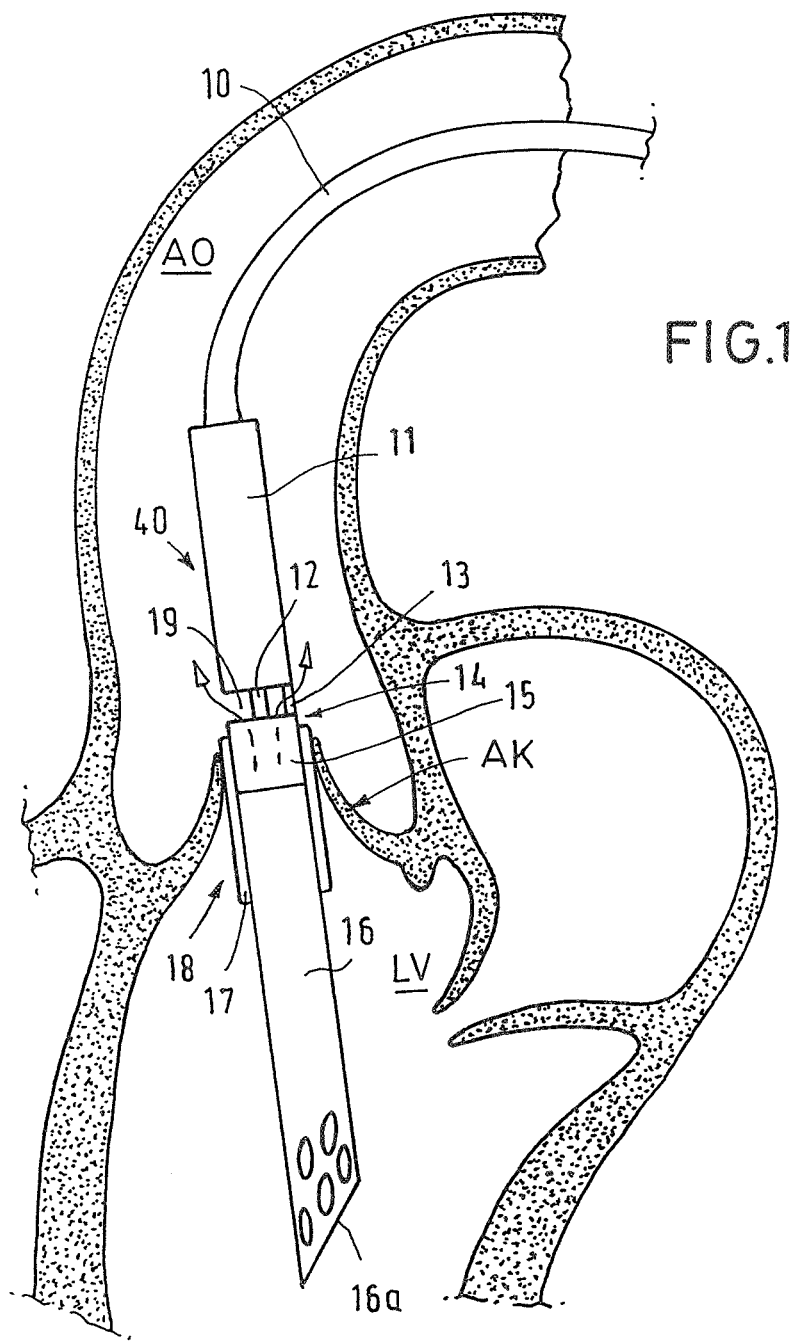

This application is a divisional of co-pending U.S. Ser. No. 10/964,066, filed Oct. 13, 2004; which is a divisional of Ser. No. 09/890,778, filed Jan. 24, 2002, now abandoned, which is in turn a 371 application of PCT/EP00/00863 filed Feb. 3, 2000; which claims priority based on German patent application 199 04 975.0 filed Feb. 6, 1999.

The invention refers to a device for intravascular cardiac surgery comprising a micro axial pump fastened to a catheter.

In WO 98/43688, an intra-cardiac blood pump is described that has a motor portion and a pump portion and can be introduced into the heart through the vascular system. Such a blood pump can be positioned in the aortal valve through the aorta, for example, to pump blood from the left ventricle into the aorta. Such blood pumps are adapted to support or replace the pumping effect of the heart. They can be positioned in the heart without requiring the heart to be opened.

From WO 97/37697, an intravascular blood pump is known that also has a motor portion and a pump portion, which are connected to a catheter. The blood pump can be pushed through the vascular system of the patient. It is a micro axial pump with a diameter of about 7 mm at most. The pump portion is surrounded by an expandable blocking device blocking the flow path outside the pump housing. Thereby, it is made sure that all blood drawn in is conveyed past the motor portion in the flow direction and short circuits caused by the flow around the pump portion are avoided. The blocking device may be an annular balloon affixed to the pump housing or an intake hose connected to the pump housing. This blood pump is intended for use in blood vessels, the blocking device only serving the purpose of blocking the vessel lumen around the pump portion, but not of deforming the vessel wall. Therefore, the balloon of the blocking device is a low pressure balloon inflated with low pressure so as to seal against the vessel wall in an non-traumatic manner.

Also known are dilating catheters having a balloon with which a vascular stenosis can be removed by pushing it open. Such dilating catheters can also be used to insert an annular stent consisting of an expandable metal structure and forming a supporting device, so as to form a permanent widening support for the stenosis. Such a dilating catheter is designed as a perfusion catheter with a pump portion for conveying blood through the inflated balloon. For cardiac valve surgery, this dilating catheter is not suitable if only for its small diameter of 2 mm at most.

The most frequent defects of cardiac valves are valvular incompetence and valves with stenoses. In case of incompetence, the valve is unable to close fully. This causes a return flow. In general, such valves have to be replaced with artificial valves. Valves with stenoses have valve leaflets grown together at the edges, whereby the valve will not open completely and does not allow the full blood flow to pass therethrough.

There are two forms of surgery on the cardiac valves: In cardiac valve replacement, the natural cardiac valve is removed and surgically replaced with a bio-prosthesis or a mechanical cardiac valve. For this type of surgery, it is necessary to keep the operating area free from blood, i.e. to divert the natural blood flow. In case of a repair of the natural cardiac valve, a minimally invasive intervention can be performed using a balloon introduced into the valve. Such operations, e.g., at the aortal valve, the cardiac surgeon or the cardiologist needs great skill. Among others, the reason for this is that the blood flow through the aorta has to be blocked during the breaking process so that the operation has to be made in very short time for the supply to the vessel system to be restored. Further, the pressure inside the heart rises extremely when blocking the aortal flow while its blood supply via the coronal vessels is halted.

It is the object of the present invention to provide a device for intravascular cardiac valve surgery with which minimally invasive valve operations can be done relatively simple and without being pressed for time.

The object is solved, according to the invention, with the features of claim 1.

In the present device, an intravascular micro axial pump is provided, i.e., a pump that can be pushed through the vascular system of a patient and has an correspondingly small outer diameter that does not exceed 8 mm. The pump portion of the micro axial pump bears a dilating device which is adapted to break up a stenosis in a cardiac valve if placed in the cardiac valve. This dilating device preferably comprises a high-pressure balloon whose expanded diameter is at least 15 mm and which is inflatable with at least 1.0 bar. The high-pressure balloon is positioned in the cardiac valve and expanded using a liquid so that it breaks or blows open a stenosis in the cardiac valve. The dilating device thus forms an active element for breaking up a stenosis in a cardiac valve, in particular a stenosis in an aortal valve or a bicuspid valve.

The lumen of the pump portion or of the cannula adjoining the pump portion is at least 8 mm so as to avoid a too strong local blood flow with large physiological volume flows of up to 7 l/min. Further, the carrier of the dilating device should have an outer diameter of at least 8 mm so that a sufficiently large support for the dilating device is formed and the extent of the diameter increase does not become excessive.

Further, the invention refers to a device for intravascularly placing a cardiac valve prosthesis according to the features of claim 5. This device is also provided with a micro axial pump bearing a dilating device. Moreover, a stent is provided carrying a flexible cardiac valve prosthesis on its inner side. The stent containing the cardiac valve prosthesis can be introduced into the pathogenic cardiac valve and can be expanded by the dilating device so that it presses the valve leaflets of the natural cardiac valve apart. This cardiac valve prosthesis includes a single- or multi-wing cardiac valve that automatically becomes functional and replaces the natural cardiac valve.

As the cardiac valve prosthesis, a jugular valve taken from calves or cows can be used. This would be a bio-prosthesis of natural tissue.

The following is a detailed description of embodiments of the invention with reference to the drawing.

Figure 2:
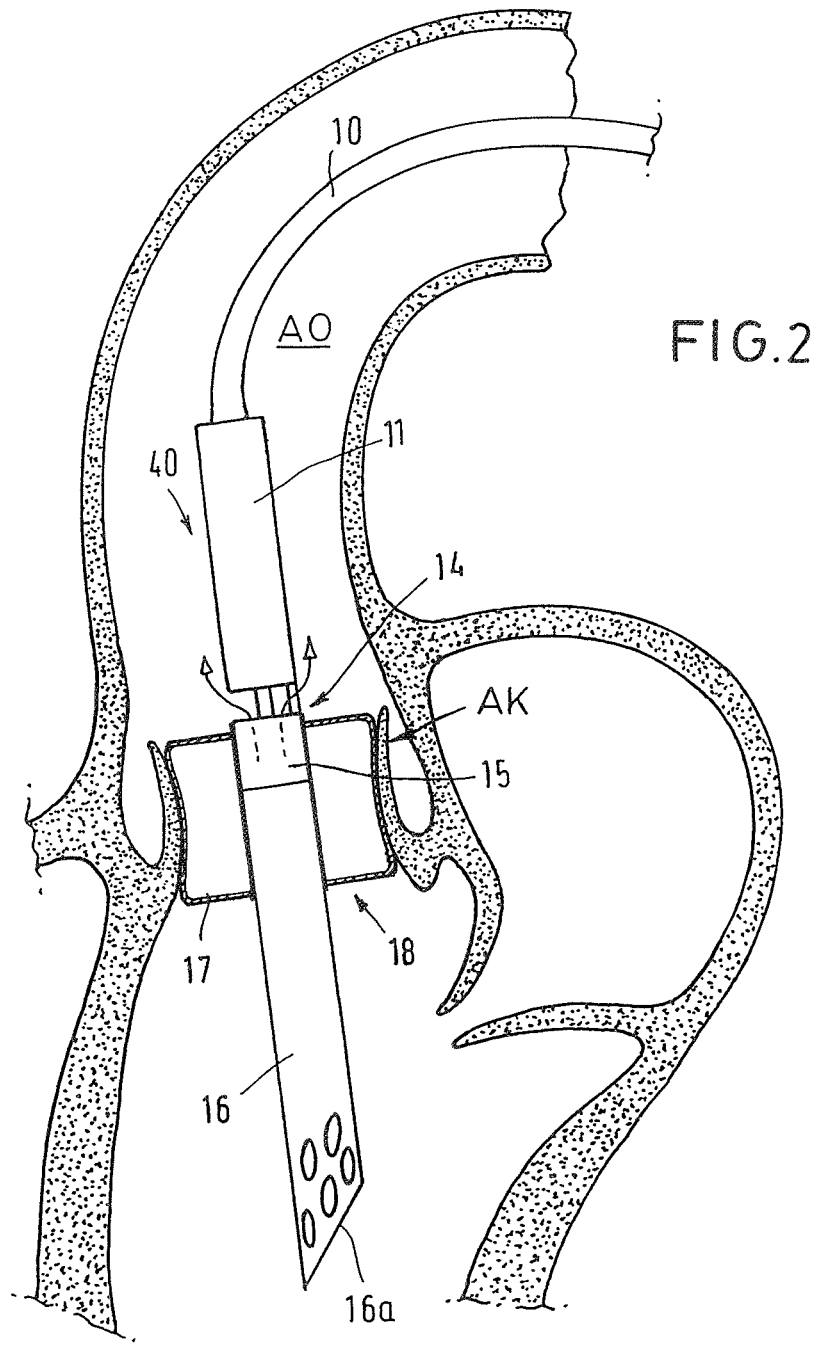
Figure 3:
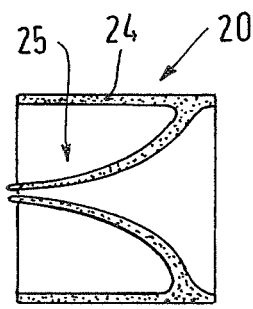
Figure 4:
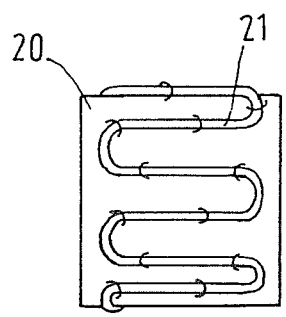
Figure 5:
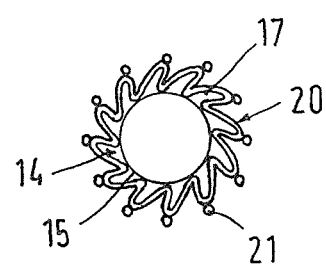
Figure 6:
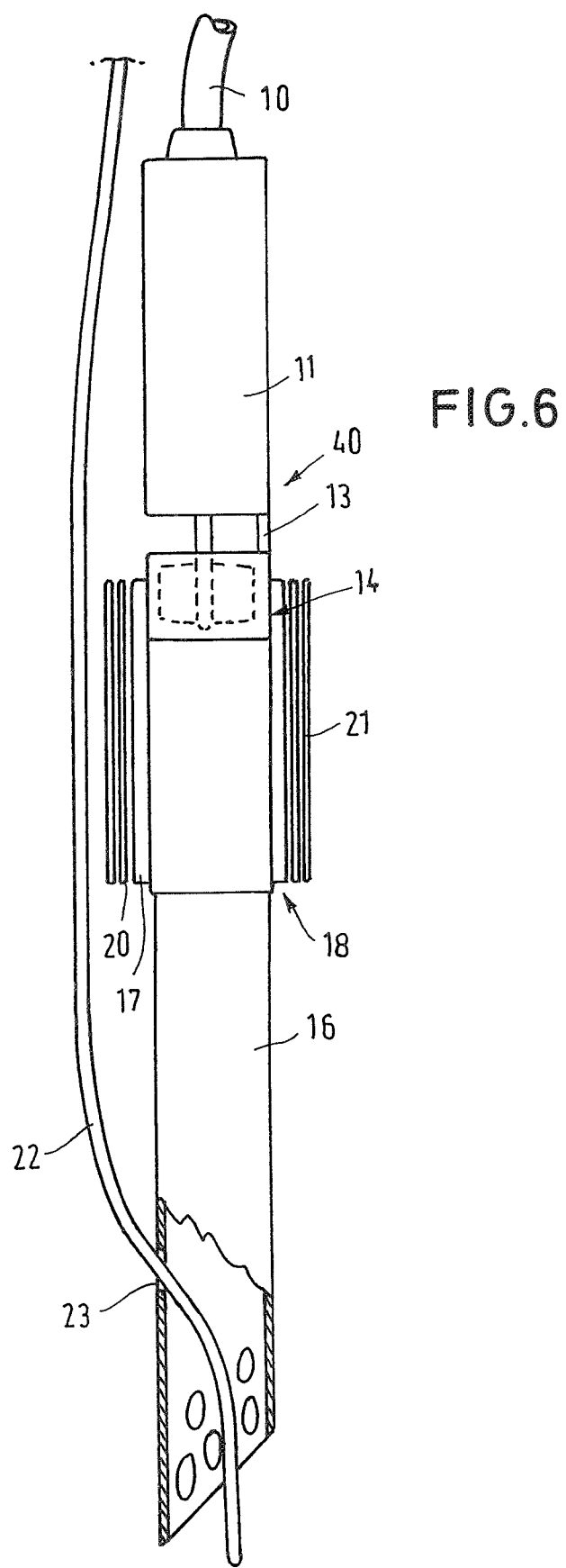
Figure 7:
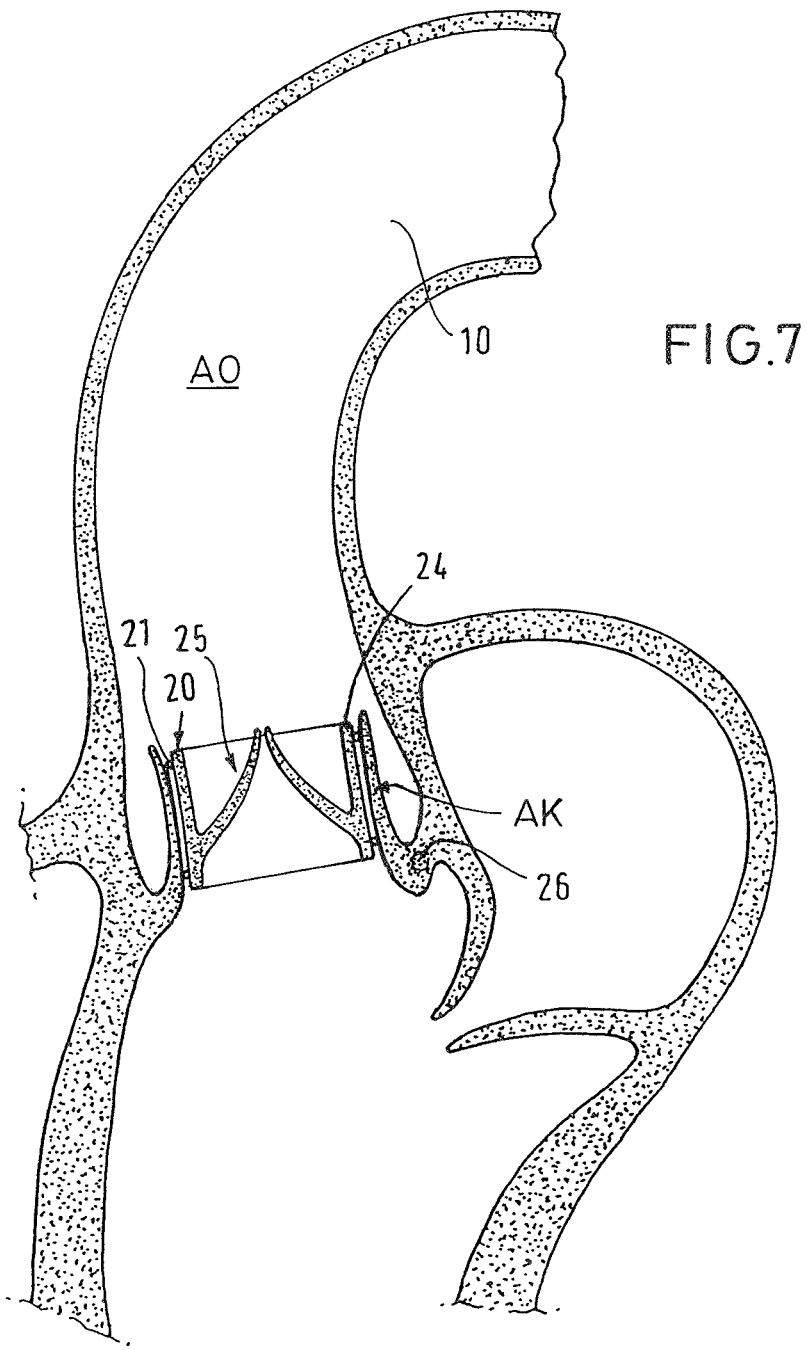

In the figures:

FIG. 1 illustrates a device for removing a stenosis in a cardiac valve, introduced into the aortal valve, FIG. 2 shows the device of FIG. 1 with the dilating device expanded, FIG. 3 is a longitudinal section of a flexible cardiac valve prosthesis, FIG. 4 illustrates the cardiac valve prosthesis of FIG. 3 in combination with an expanded stent, FIG. 5 is a cross-sectional view of the pump portion with a surrounding balloon as well as a stent with a cardiac valve prosthesis contained therein that is also folded, FIG. 6 is a view of the device for implanting the flexible cardiac valve prosthesis, and FIG. 7 shows the region of the heart with the implanted cardiac valve prosthesis in an aortal position.

FIG. 1 illustrates a part of the heart, namely the left ventricle LV, from which blood flows through the aortic valve into the aorta AO. The aortic valve has three valve leaflets projecting into the aorta AO and forming a check valve in a fluidic sense that allows passage only into the aorta.

To push open an aortic valve AK with a stenosis, the device illustrated in FIG. 1 is introduced into the heart through the aorta. This device comprises a catheter 10 connected with a micro axial pump 40. The pump comprises a drive portion 11 including an electric motor and driving a shaft 12 protruding from the distal end of the cylindrical drive portion 11. A holding web 13 extends axially from the drive portion 11 to the tubular pump portion 14. The pump portion 14 comprises a pump ring 15 including an impeller wheel driven by the drive shaft 12, and a cannula 16 axially continuing the pump ring 15. The entire pump device, namely the drive portion 11 and the pump portion 14, has a maximum diameter of 8 mm. The catheter 10 comprises the electric wires for the supply and the control of the micro axial pump 40 and a pressure lumen through which pressure liquid can be supplied.

An annular balloon 17 is provided on the pump portion 14 and is illustrated in FIG. 1 in a folded state. Through the pressure lumen of the catheter 10, the balloon 17 may be inflated with liquid. The balloon is a high-pressure balloon with an inflated diameter of at least 15 mm, preferably between 15 and 40 mm, and resistant to pressures up to 8 bar. The balloon 17 extends over a pat of the length of the cannula 16. Its entire length may be supported by a rigid ring that prevents a compression of the cannula 16.

The pump device is introduced into the aorta by first placing a guiding wire (not illustrated) in the aorta and the left ventricle. Then the device is advanced along the guiding wire and positioned in the aortic valve AK such that the intake portion 16a is within the left ventricle LV, whereas the outlet portion 19 is within the aorta. The pump portion 15 is thus enclosed by the aortic valve AK. The pump device conveys backward, i.e., it draws axially and ejects laterally in the outlet portion 19.

After the pump device has been positioned in the way illustrated in FIG. 1, the drive portion 11 is activated so that the pump conveys blood from the left ventricle LV into the aorta AO. Thereby, the heart is relieved in terms of volume and pressure and is calmed down. Then, the balloon 17 forming the dilating device 18 is inflated and expanded in the middle of the aortic valve AK. By the high-pressure inflated balloon 17, the valve leaflets of the aortic valve AK are pushed open and possible adhesions to the commissures are broken. In this manner a valve with a stenosis is pushed open far enough to reassume a completely open state. With the pump device, this form of valve operation can be performed in a calmed environment and without haste since, for the duration of the surgery, the cardiac output (l/min) is conveyed by the pump device through the dilating device. In a similar manner, the above described dilating device can be used to break open a natural bicuspid valve with a stenosis.

FIGS. 3 to 7 refer to a device with which an insufficient valve is replaced with a valve prosthesis. To this end, generally the same device as described with reference to FIGS. 1 and 2 is used. This device is illustrated in FIG. 6. Situated on the deflated and folded dilating device 18 is a flexible cardiac valve prosthesis 20 above which a compressed spiral-shaped stent 21 is located.

FIG. 6 further illustrates the guiding wire 22 that serves to advance the device with the catheter 10 and to place it in the correct position. The guiding wire 22 projects from the distal end of the cannula 16. It passes through a lateral hole 23 in the cannula and extends outside the pump portion 14 and the drive portion 11 along the catheter 10.

The flexible cardiac valve prosthesis 20 is illustrated in FIG. 3. It is a bio-prosthesis that has been taken from a cow or a calf. For this purpose, a section 24 of a blood vessel including a vascular valve 25 was removed. This valve 124 may be a single-wing or a three-wing valve. According to FIG. 4, this valve prosthesis 20 is placed within a stent 21. The stent 21 is a tubular element of metal rods which, in the present example, are bent meander-like and allow for an axial compression or radial expansion. Other stent structures could also be used, such as, for example, a cell structure of stretch material. It is essential that the stent can reliably assume a compressed tubular shape and an expanded tubular shape. The hose-shaped wall 24 of the vascular prosthesis 20 is sewed to the rods of the stent 21. Thus, the vascular prosthesis 20 is fastened to the inner side of the stent 21 so that after implantation of the vascular prosthesis, the stent rests between the natural cardiac valve and the bio-prosthesis and has no contact with the blood. Thus, the stent does not require the application of anti-coagulants against thrombosis.

FIG. 5 illustrates the pump portion 14 with the pump ring 15. The balloon of the dilating device 18 and the valve prosthesis 20 are folded in a plurality of loops around the pump ring 15, the valve prosthesis being affixed to the rods of the stent 21. In this state, the balloon, the valve prosthesis 20 and the stent 21 form a flat package surrounding the pump portion 14. This package is positioned in the natural cardiac valve AK. Thereafter, the pump is activated and the dilating device 17 is inflated with the pump operating. The stent 21 is dilated, widening the cardiac valve prosthesis 24 and pressing the leaflets of the natural aortic valve AK outward into the open position (systolic valve position, as illustrated in FIG. 7. Thereby, the aortic valve AK is passivated. The stent 21 remains in the cardiac valve opening. In the stent, there is the cardiac valve prosthesis 24 enlarged to its original state and including the valve leaflets 25. This cardiac valve now assumes the function of the natural aortic valve AK.

To avoid displacement of the cardiac valve prosthesis, the stent 21 or the cardiac valve prosthesis 20 can be fixed in the annulus 26 surrounding the natural cardiac valve. This is a strong ring of cartilage suitable for use as a holder of a cardiac valve prosthesis.

The invention claimed is:

1. A method for performing intravascular cardiac surgery in a heart having a pressure, a volume and a cardiac output, the method comprising:
   providing a micro axial pump fastened to a catheter and having a tubular pump portion with an intake portion and an outlet portion and a dilating device thereon;
   providing a flexible cardiac valve prosthesis;
   mounting said flexible cardiac valve prosthesis in a folded condition within a tubular expandable stent;
   placing said stent on said tubular pump portion such that said cardiac valve is situated on said dilating device;
   positioning said micro axial pump in the aortic valve of a patient heart such that said intake portion is within the left ventricle of the patient heart, while said outlet is within the aorta;
   driving the micro axial pump at a rate sufficient to relieve the heart of excessive blood volume and pressure caused by the positioning of the pump with the stent and valve prosthesis mounted thereto in the aortic valve, wherein the micro axial pump conveys the cardiac output; and expanding said tubular stent radially, to thereby break open a stenosis in the natural cardiac valve and position and fix said stent with said cardiac valve prosthesis within the aortal valve.

2. The method of claim 1, wherein said cardiac valve prosthesis is a bio prosthesis taken from an animal and comprising a section of a blood vessel including a vascular valve.

3. The method of claim 1, wherein the step of positioning the micro axial pump in the aortal valve of the patient is carried out via the aorta.

4. The method of claim 1, wherein said dilating device comprises a high-pressure balloon that is inflatable with a pressure of at least 1.0 bar.

5. The method of claim 1, wherein said dilating device comprises a high-pressure balloon that is resistant to pressures up to 8.0 bar.

\* \* \* \* \*